United States Patent [19]

McGuire et al.

[11] Patent Number: 5,374,270

[45] Date of Patent: Dec. 20, 1994

[54] DEVICE AND METHOD FOR INSERTION OF GUIDE PIN

[75] Inventors: David A. McGuire, 3418 Lakeside Dr., Anchorage, Ak. 99515; Stephen D. Hendricks, Anchorage, Ak.

[73] Assignee: David A. McGuire, Anchorage, Ak.

[21] Appl. No.: 942,667

[22] Filed: Sep. 9, 1992

Related U.S. Application Data

[63] Continuation-in-part of Ser. No. 806,906, Dec. 13, 1991, Pat. No. 5,257,996.

[51] Int. Cl.$^5$ .................. A61B 17/00; A61F 5/00; A61F 2/32
[52] U.S. Cl. .................. 606/86; 606/86; 606/104
[58] Field of Search .............. 606/72, 73, 65, 96, 606/97, 98, 61, 104

[56] References Cited

U.S. PATENT DOCUMENTS

| | | | |
|---|---|---|---|
| 2,952,254 | 9/1960 | Keating | 606/75 |
| 3,554,193 | 1/1971 | Konstantinou | 606/65 |
| 4,278,091 | 7/1981 | Borzone | 606/75 |
| 4,830,000 | 5/1989 | Shutt | 606/80 |
| 4,988,351 | 1/1991 | Paulos | 606/72 |
| 5,190,548 | 3/1993 | Davis | 606/80 |

FOREIGN PATENT DOCUMENTS

| | | | |
|---|---|---|---|
| 0451932 | 10/1991 | European Pat. Off. | 606/73 |
| 3701765 | 6/1988 | Germany | 606/73 |

*Primary Examiner*—Michael A. Brown
*Attorney, Agent, or Firm*—Bromberg & Sunstein

[57] ABSTRACT

A method of inserting a guide pin into tissue including inserting into the tissue a device having a cannula disposed longitudinally therein, a shank, and a tip. A guide pin movably disposed in the cannula and having a shank end proximal to the shank of the drill bit and a tip proximal to the tip of the drill bit. A retaining means associated with at least one of the drill bit and the guide pin for permitting the releasable retention of the guide pin in the cannula by means of adjustable force exerted on the guide pin by the drill bit.

7 Claims, 3 Drawing Sheets

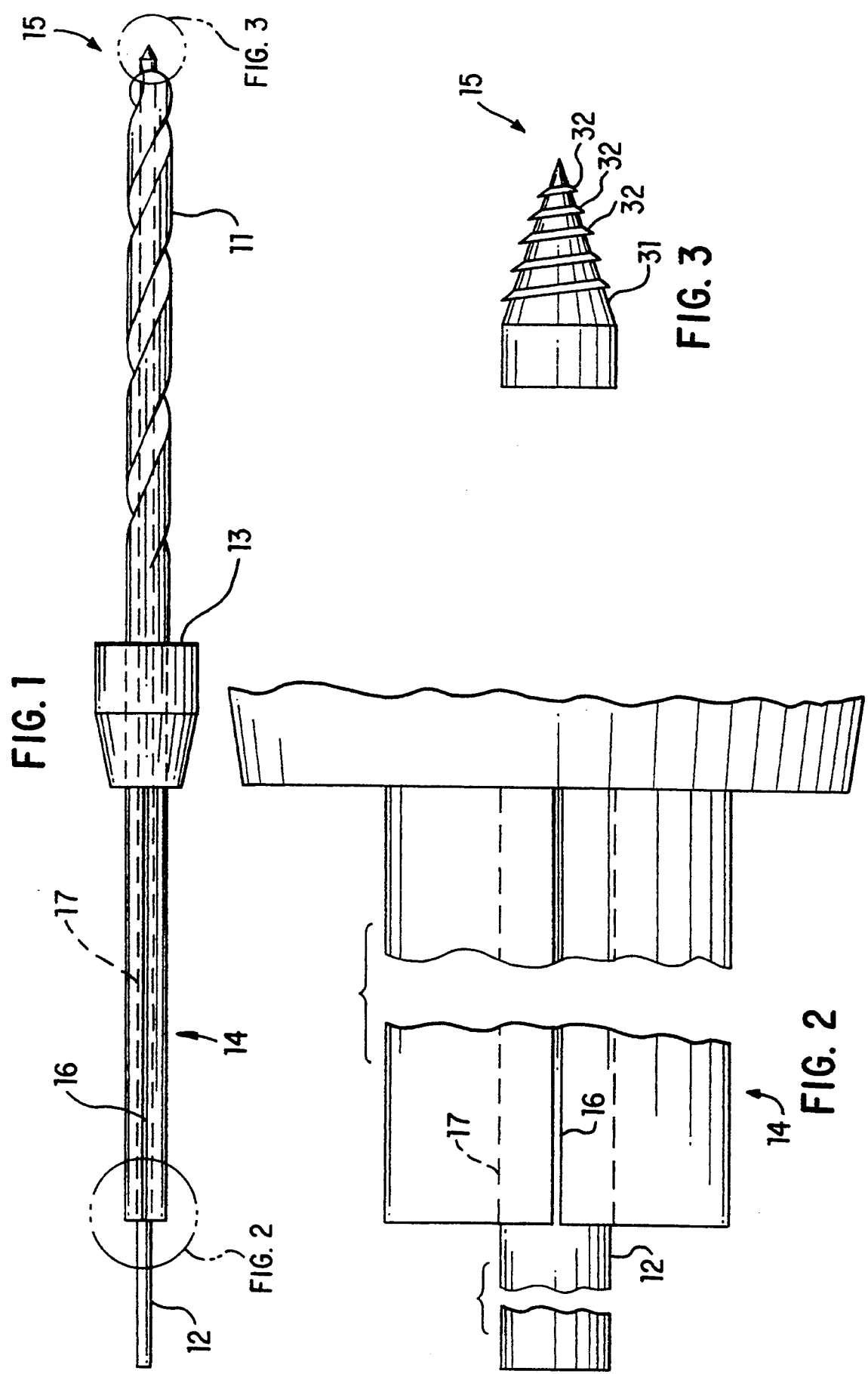

DEVICE AND METHOD FOR INSERTION OF GUIDE PIN

The present application is a continuation in part of U.S. application Ser. No. 07/806,906, filed Dec. 13, 1991, now U.S. Pat. No. 5,257,996, issued Nov. 2, 1993, for an invention of applicant entitled "Surgical Pin Passer"; this related application is hereby incorporated herein by reference.

TECHNICAL FIELD

The present invention relates to methods and devices for the insertion of guide pins into biological tissue, particularly bone, as well as to the affixation of material, such as ligaments or other tissue or prostheses, to bone.

BACKGROUND ART

In the case of fixation of fractures of the femoral neck, it is known to employ a tool that includes a guide pin positioned inside of a sleeve. U.S. Pat. No. 4,450,835, issued for an invention of Asnis et al. The two components are configured to function in cooperation with one another at one end like a drill bit, so that the tool can be inserted in bone, and the sleeve then withdrawn, leaving the guide pin in place. Col. 2, line 57, to col. 3, line 68; col. 5, line 36 to col. 8, line 35. The guide pin can then serve to position cannulated screws in the bone. The guide pin is apparently retained in the sleeve solely by action of a Trinkle fitting in a surgical drill, col. 5, lines 55–56, and col. 6, lines 51–58, yet its surrounding sleeve apparently can be dislodged after removal of the tool from the fitting only by tapping the guide pin forward in the sleeve with a mallet, col. 7, lines 53–56, a procedure that may encounter some difficulty depending on the relative position in bone of the drilling ends of the sleeve and the guide pin. The tool is said, without explanation, to be applicable to any surgical procedure involving insertion of a guide pin for a cannulated surgical implant. Col. 3, lines 62–65.

The repair of a ligament tear (for example, a collateral ligament tear) frequently involves the need to affix a ligament to bone. Currently both staples (which may be metal or of an absorbable material such as polylactic acid) and washered screws are used for this purpose. Staples, while apparently convenient, may not provide as secure an affixation as screws, while screws are difficult to use. The convenience of staples may in fact be somewhat illusory, since it is recommended, for example, in the case of many staples to drill pilot holes for each staple leg.

The affixation by washered screws requires predrilling through both the ligament and the bone, a procedure requiring typically that the ligament be held in place during the entire drilling period, and thereafter while removing the drill and inserting the screw. However, it is difficult to hold the ligament in place during the entire time required by such a procedure. Moreover, because ligaments have directional fiber bundles, these bundles tend to separate to a certain degree dependent upon any force exerted on the bundle in the axial direction (that is in the direction of the pilot hole for the screw). When the pilot hole drill is removed, the fiber bundles tend to close back together again, making the visual location of the pilot hole center difficult at best.

One approach to dealing with the problem involves seeking to insert a guide pin quickly into the pilot hole immediately after the drill bit is removed; the screw is then inserted either over the guide pin (in case the screw is cannulated) or beside the guide pin (in case the screw is not cannulated). However, this approach is not always successful, nor is it easy.

Washers have been employed to prevent the ligament from wrapping around the head of the screw as it approaches maximum torque application and to assist in distribution of the forces from the screw head more evenly across the ligament. However these washers are prone to rotation and the ligament moves underneath the washer.

SUMMARY OF THE INVENTION

In a preferred embodiment, the invention provides a device for insertion of a guide pin in biological tissue, such as bone. The embodiment includes a cannulated drill bit with a guide pin disposed in the cannula. The problem of easy removal of the drill bit (while leaving the guide pin in place) is solved in this embodiment by providing an arrangement, associated with at least one of the drill bit and the guide pin, for permitting the guide pin to be retained releasably in the cannula by means of adjustable forces exerted on the guide pin by the drill bit. In one implementation of such an arrangement, the shank of the drill bit includes one or more longitudinal slots, so that when the bit-with-guide-pin combination is tightened in a drill chuck, the drill bit transmits to the guide pin the retaining forces of the chuck, causing the cannula wall of the drill bit to grip the guide wire by forces dependent on how tightly the chuck is gripping the shank of the bit. In another implementation of such an arrangement, the outside of the guide pin and the cannula wall of the drill bit are provided with mating threads, so that the guide pin is threaded into the drill bit. The threads are established in a direction to cause the two components to be tightened into one another during ordinary drilling, and to tend to cause the two components to be loosened from one another when the drill's direction of rotation is reversed for the purpose, for example, of backing the drill out of the bone after drilling is completed.

In a further embodiment of a device in accordance with the invention, regardless of the arrangement for retaining the pin in the bit, the tip of the pin is provided with an arrangement for grabbing the tissue. In one embodiment, the tip is tapered and provided with threading.

In another embodiment, the invention provides a device for fastening material, including biological tissue (such as a torn ligament) and a prosthesis to bone. The device includes a cannulated screw and a washer; the washer has on the side facing the material an arrangement for preventing rotation of the washer relative to the material when the screw is screwed into the bone. In one implementation, the arrangement includes a series of spikes projecting axially away from the material side of the washer.

The invention also provides methods of inserting a guide pin into tissue and of affixing material to bone using embodiments of the devices described above.

BRIEF DESCRIPTION OF THE DRAWINGS

The foregoing features of the invention will be more readily understood by reference to the following description, taken with the accompanying drawings, in which:

FIG. 1 is a side elevation of a cannulated drill bit with guide pin in accordance with a preferred embodiment of the invention;

FIG. 2 is detail of the shank end of the embodiment of FIG. 1;

FIG. 3 is detail of the tip end of the embodiment of FIG. 1;

DETAILED DESCRIPTION OF SPECIFIC EMBODIMENTS

Figure 5:
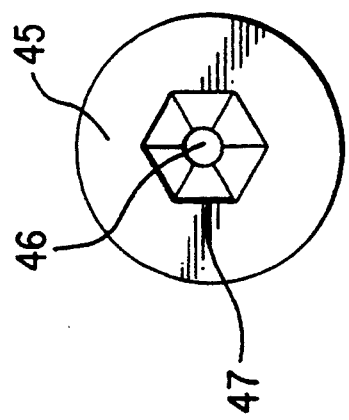
FIG. 5 is a top view of the screw of FIG. 4.

In FIG. 1 is shown a cannulated drill bit 11 with guide pin 12 in accordance with a preferred embodiment of the present invention. The bit includes a cannula 17 oriented longitudinally in which the guide pin is movably disposed. The drill bit, which includes a shank 14 and a tip 15, is here provided with stop 13 to restrict forward axial motion of the drill into tissue.

As shown in further detail in FIG. 2, the shank 14 end of the drill bit includes one or more longitudinal slots 16. The slots permit inward radial motion of the shank when the shank is inserted into a drill chuck and the chuck is tightened. In this manner, when the bit-with-guide-pin combination is tightened in the drill chuck, the drill bit transmits to the guide pin the retaining forces of the chuck, causing the cannula wall of the drill bit to grip the guide wire by forces dependent on how tightly the chuck is gripping the shank of the bit. Preferably the shank 14 of the bit 11 is made of sufficiently resilient material (for example, an appropriate alloy of steel) so as to return to its original shape when the shank is removed from the chuck, so as to facilitate removal of the drill bit from the guide pin. Although the choice of such a material may affect the hardness of the drill tip 15 and therefore life of the drill, the tip 15 may be made of a different alloy, and, if desired, linked to the material of the shank 14 at the location of the stop 13, where the drill bit 11 may be reinforced. Alternatively, the drill bit may be disposed of after use has dulled it.

Although the embodiment shown here utilizes a slot in the shank 14 of the drill bit 11 to achieve ready removability of the drill bit from the guide pin 12, other alternatives are possible. For example, the outside of the guide pin and the cannula wall of the drill bit may be provided with mating threads, so that the guide pin is threaded into the drill bit. Such threads are preferably located near the tip 15 of the drill bit 11, so as to minimize the travel of the threads of the guide pin 12 in the cannula 17. The threads are established in a direction to cause the two components (guide pin and drill bit) to be tightened into one another during ordinary drilling, and to tend to cause the two components to be loosened from one another when the drill's direction of rotation is reversed for the purpose, for example, of backing the drill out of the bone after drilling is completed. In the case of both retaining arrangements described, the arrangement permits the releasable retention of the guide pin in the cannula by means of adjustable forces exerted on the guide pin by the drill bit.

As shown in further detail in FIG. 3, the guide pin 12 is provided with a taper 31 and threading 32. In this manner, it is provided with an arrangement for grabbing the bone tissue as the combination bit 11 and guide pin 12 are drilled into the bone, so that when the drill bit is removed from the chuck and pulled from the guide pin, the guide pin will tend to remain in the bone.

In the embodiment herein, the guide pin is approximately 12 mm longer than its respective drill bit. For a cannulated screw that is 4.5×40 mm, the drill bit has a diameter of about 3 mm and a length from the tip end to the stop 13 of 40 mm. The stop occupies about 10 mm, and the shank is another 30 mm. The tip of the guide pin protrudes about 2 mm from the tip 15 of the drill bit. The diameter of the guide pin is small enough to fit comfortably within the cannula of the cannulated screw being used. When the cannulated screw is made of polylactin acid or other bioabsorbable material, the need for structural strength of the screw dictates use of a small cannula, so that a guide pin of 0.0450 inches (1.1 mm) is suitable for a typical 45×40 mm screw. However, such a screw may utilize an even smaller cannula, for example 0.0394 inches (1 mm), in which case, a guide pin of the order of 0.0380 inches (0.965 mm) is suitable. The dimensions provided here may be readily adapted to accommodate other sizes of cannulated screws. Of course, a longer drill portion of the drill bit from tip to stop will permit use of a longer cannulated screw.

Figure 6:
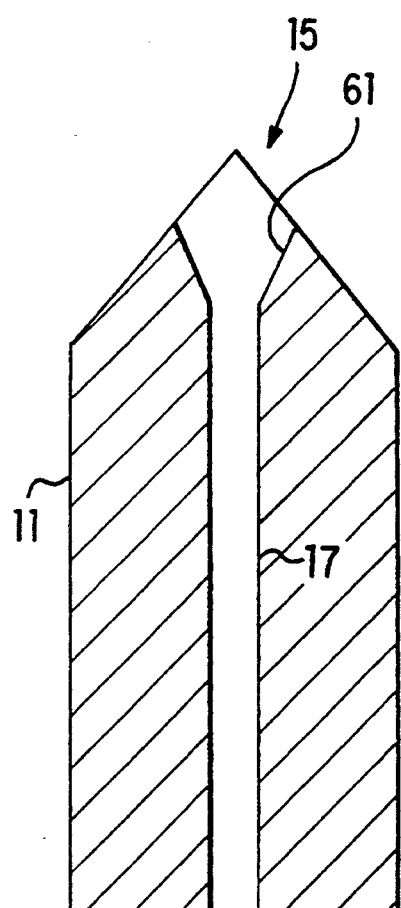
FIG. 6 and 7 illustrate a further embodiment of the device of FIG. 1 in which the guide pin is prevented during insertion from traveling too far into the drill bit.
Figure 7:
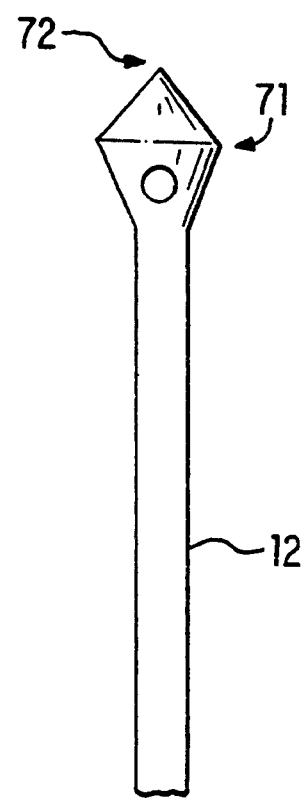

If desired, the guide pin may be fitted with a suitable stop near the tip to prevent accidental axial motion of the guide pin toward the drill into the drill bit. FIGS. 6 and 7 illustrate such an arrangement. The tip 72 of guide pin 12 includes an expanded region 71 formed with a double bevel, and the cannula 17 of the drill bit 11 terminates at the tip 15 of the drill bit in a region 61 shaped to conform with the corresponding portion of the region 71 of the guide pin. The guide pin must be shaped in relation to the cannulated screw so that the diameter of the expanded region 71 is smaller than the diameter of the cannula in the screw. The guide pin may be made of any suitable material, including stainless steel and nitinol.

The shank end of the guide pin protrudes about 10 mm from the shank end of the drill bit, and this exposed portion may be used to maintain the position of the guide pin during the extraction of the drill bit. This portion may be used to tap the guide pin further into the bone than the predrilled depth of the hole provided by the drill bit; alternatively, or in addition, this portion may be used to grasp the pin with a clamp while extracting the drill bit from its position in the hole.

Thus the embodiments described may be used in a drill chuck to form a hole in tissue, and thereafter, the chuck of the drill is loosened, and the assembly removed from the chuck. The drill bit is then extracted from the hole, leaving the guide pin still in the hole.

Figure 4:
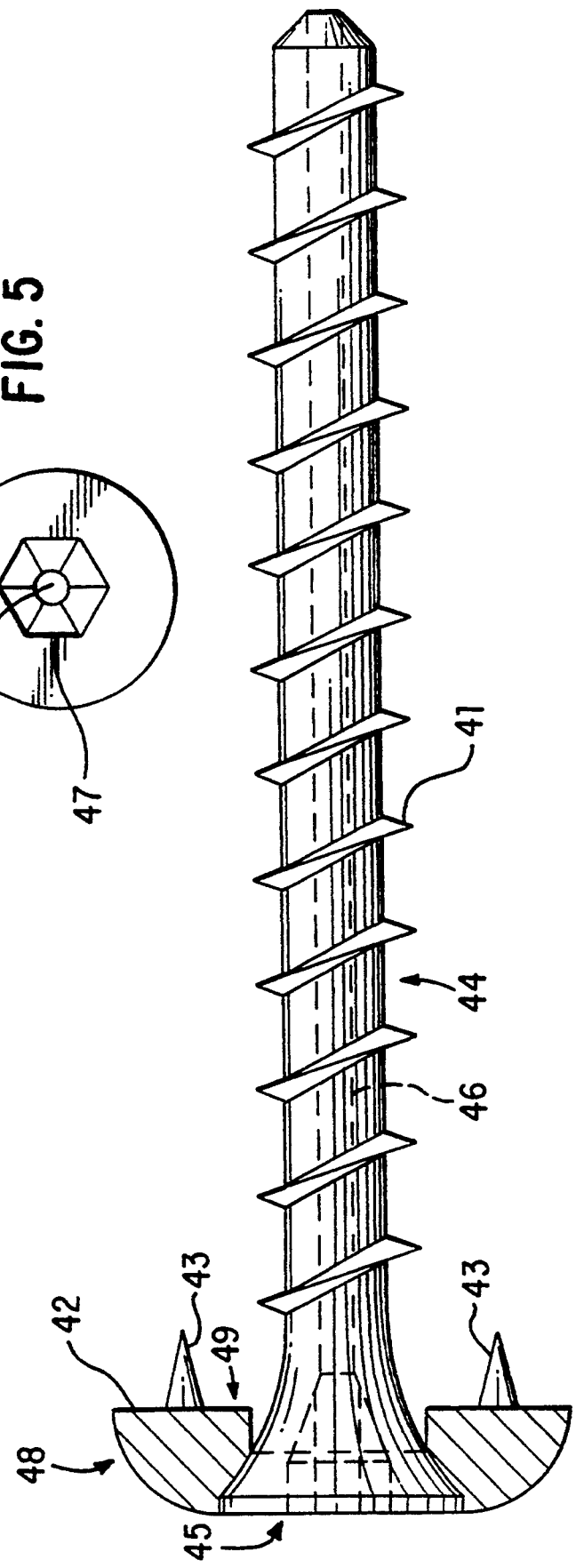
FIG. 4 is a side elevation of a cannulated screw and washer in accordance with a preferred embodiment of the present invention.

The guide pin may be used to guide into location, for example, a cannulated screw 41 and washer 42 combination such as shown in FIG. 4. (It will be understood, however, that the guide pin may also be used for any other purpose known in the art.) The screw 41 is provided with a cannula 46 about 1 mm in diameter and includes a body 44 that is approximately 40 mm in length, and a flat head 45 that is about 4.5 mm in diameter. The head is joined to the body by a gooseneck, and is fitted, as shown in FIG. 5, with a receptacle 47 for a hex wrench. The thread's outside diameter is about 4.5 mm and the inside diameter about 3 mm. The washer is shaped so that its aperture passes the body 44 but not the head 45 of the screw. The washer 42 has a screw head side 48 and a material side 49. The material side is provided with an arrangement for preventing rotation of the washer relative to the material when the screw is screwed into bone. In this embodiment, the arrangement includes a series of spikes protruding axially away from the material side of the washer. The spikes are typically of the order of 2.2 mm, although their size, like that of the washer, and of the screw, is subject to variation in accordance with the particular application. The screw may typically range up to twice the diameter and length described herein. In some embodiments it may be desirable to make the screw and washer out of polylactic acid or other bioabsorbable material.

In repair of a collateral ligament tear, the embodiment of FIG. 1 may be used to drill a pilot hole for the screw while holding the ligament in place, so that the hole is formed in both the ligament and the bone. The drill bit 11 may then be extracted from the hole while leaving the guide pin 12 in place as described above. Thereafter, the cannulated screw 41 and washer 42 are inserted with the guide pin 12 in the cannula 46, and the spikes 43 facing toward the ligament. The screw is then tightened to hold the ligament in place.

It will be apparent that the devices and methods of the present invention are not limited to the repair of collateral ligament tears. They are suitable for a wide range of attachments to bone, including the joining of tendons, other bones, and prostheses to bone.

What is claimed is:

1. A method of inserting a guide pin into tissue comprising:
    (1) inserting into the tissue a device including
        (a) a drill bit having a cannula disposed longitudinally therein, a shank, and a tip;
        (b) a guide pin, movably disposed in the cannula, and having a shank end proximal to the shank of the drill bit and a tip proximal to the tip of the drill bit; and
        (c) retaining means, associated with at least one of the drill bit and the guide pin, for permitting the releasable retention of the guide pin in the cannula by means of adjustable forces exerted on the guide pin by the drill bit;
    (2) releasing the drill bit from retaining the guide pin; and
    (3) removing the drill bit from the bone, leaving the guide pin remaining in the tissue.

2. A method of inserting a guide pin into tissue comprising:
    (1) inserting into the tissue a device including
        (a) a drill bit having a cannula disposed longitudinally therein, a shank, and a tip;
        (b) a guide pin, movably disposed in the cannula, and having a shank end proximal to the shank of the drill bit and a tip proximal to the tip of the drill bit;
        (c) retaining means, for releasably retaining the guide pin in the cannula; and
        (d) grabbing means for grabbing tissue, disposed near the tip of the guide pin;
    (2) releasing the drill bit from retaining the guide pin; and
    (3) removing the drill bit from the tissue, leaving the guide pin remaining in the tissue.

3. A method of affixing material to bone comprising:
    (1) inserting a guide pin through both the material and the bone by using a device including a cannulated drill provided with a releasably retained guide pin to form a hole through both the material and the bone and releasing the guide pin from the cannulated drill to leave the guide pin in the hole;
    (2) providing
        (a) a cannulated screw having a head and a body; and
        (b) a washer, having a material side and a screw head side and a central aperture having a central axis, the washer being shaped so that the aperture passes the body but not the head of the screw;
        the washer having, on the material side, stabilization means for preventing rotation of the washer relative to the material when the screw, with washer thereon and the material side of the washer facing the material, is screwed into bone;
    (3) inserting the screw, with washer thereon and the material side of the washer facing the material, on the guide wire; and
    (4) tightening the screw.

4. A method according to claim 3, wherein step (1) includes the step of using a device in accordance with claim 1.

5. A method according to claim 3, wherein step (1) includes the step of using a device in accordance with claim 10.

6. A method of affixing material to bone comprising:
    (1) utilizing a cannulated drill bit fitted with a guide pin releasably retained therein to form a hole through both the material and the bone;
    (2) withdrawing the drill bit from the hole, leaving the guide pin in place in the hole;
    (3) providing a cannulated screw having a head and a body;
    (4) inserting the screw on the guide wire; and
    (5) tightening the screw.

7. A method according to claim 6, wherein step (1) includes the step of using a device including the cannulated drill bit, the guide pin movably disposed in the cannula of the drill bit and retaining means, associated with at least one of the drill bit and the guide pin, for permitting the releasable retention of the guide pin in the cannula by means of adjustable forces exerted on the guide pin by the drill bit.

* * * * *